United States Patent
Kholkar et al.

(10) Patent No.: US 12,197,902 B2
(45) Date of Patent: Jan. 14, 2025

(54) METHOD AND SYSTEM FOR LEARNING BASED DYNAMIC SOFTWARE SYSTEM ADAPTATION

(71) Applicant: Tata Consultancy Services Limited, Mumbai (IN)

(72) Inventors: Deepali Dinanath Prabhu Kholkar, Pune (IN); Suman Roychoudhury, Pune (IN); Sreedhar Sannareddy Reddy, Pune (IN); Vinay Kulkarni, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 158 days.

(21) Appl. No.: 18/112,004

(22) Filed: Feb. 21, 2023

(65) Prior Publication Data

US 2023/0266951 A1    Aug. 24, 2023

(30) Foreign Application Priority Data

Feb. 20, 2022   (IN) ............................. 202221007955

(51) Int. Cl.
*G06F 8/41* (2018.01)
*G06F 8/656* (2018.01)
*G06F 8/77* (2018.01)

(52) U.S. Cl.
CPC .............. *G06F 8/443* (2013.01); *G06F 8/656* (2018.02); *G06F 8/77* (2013.01)

(58) Field of Classification Search
None
See application file for complete search history.

(56) References Cited

U.S. PATENT DOCUMENTS 11,574,243 B1 * 2/2023 Mallya Kasaragod ..................... G06F 9/5044
2017/0153967 A1 * 6/2017 Kalech ................ G06F 11/3664
(Continued)

FOREIGN PATENT DOCUMENTS

CA        2970249 A1    12/2018

OTHER PUBLICATIONS

Abufouda, "Quality-aware Approach for Engineering Self-adaptive Software Systems," (2014).
(Continued)

*Primary Examiner* — Qing Chen
(74) *Attorney, Agent, or Firm* — Finnegan, Henderson, Farabow, Garrett & Dunner, LLP (57) ABSTRACT

The present disclosure provides a dynamic functional adaptation of software systems based on real time need, which is unaddressed by the conventional methods. Initially, the system receives an output generated by a software system under execution corresponding to a given input. Further, a deviation in the generated output is identified based on a comparison between the generated output and a corresponding expected output. Further, an optimal policy is identified based on the generated output and the identified deviation using a reward based Reinforcement Learning (RL) model. Further, an adaptation specification is generated based on the identified optimal policy using an Adaptation Specification Generation (ASG) technique, Further, a software code is generated dynamically for the identified optimal policy using an ASG based code generation technique. Finally, the software system under execution is updated dynamically by calling a method corresponding to the generated software code and executing the software system.

18 Claims, 3 Drawing Sheets

(56) References Cited

U.S. PATENT DOCUMENTS

2020/0082257 A1* 3/2020 Qiao .................. G06N 3/047
2022/0083842 A1* 3/2022 Achar ................. G06N 3/048
2023/0333830 A1* 10/2023 Amoros ............... G06F 8/658

OTHER PUBLICATIONS

Cacciagrano et al., "Healthcare Tomorrow: Toward Self-adaptive, Uniquitous and Personalized Services," (2011).
Palm et al., "Online Reinforcement Learning for Self-Adaptive Smart IoT Systems," (2021).

* cited by examiner

METHOD AND SYSTEM FOR LEARNING BASED DYNAMIC SOFTWARE SYSTEM ADAPTATION

PRIORITY CLAIM

This U.S. patent application claims priority under 35 U.S.C. § 119 to: India application No. 202221007955, filed on Feb. 20, 2022. The entire contents of the aforementioned application are incorporated herein by reference.

TECHNICAL FIELD

The disclosure herein generally relates to the field of software engineering and, more particularly, to a method and system for learning based dynamic software system adaptation.

BACKGROUND

In modern days real time applications like banking, ecommerce and healthcare systems are being subjected to an unprecedented variety of change drivers such as new regulations, emerging business models, and changing needs of stakeholders which couldn't be predicted earlier. This creates new demand on enterprises to meet stated goals in a dynamic and uncertain environment that translates to demands on the enterprise's software systems. Even, the goals too may change over time as enterprises look to exploit emerging opportunities in the changing environment.

Conventional real time software applications are introducing changes manually which is a time-consuming, and expensive task. Some other conventional software adaptation architectures can adapt only non-functional requirements (NFRs) of software like latency, response time and performance using a static repository of knowledge. Functional adaptation of software systems based on real time need, in a dynamic uncertain environment, by continuously refining the knowledge remains mostly unaddressed.

SUMMARY

Embodiments of the present disclosure present technological improvements as solutions to one or more of the above-mentioned technical problems recognized by the inventors in conventional systems. For example, in one embodiment, a method for learning based dynamic software system adaptation is provided. The method includes receiving, by one or more hardware processors, an output generated by a software system under execution corresponding to a given input, wherein the software system under execution comprises a plurality of states, a plurality of events, a plurality of conditions, a plurality of actions and a plurality of goals. Further, the method includes identifying, by the one or more hardware processors, a deviation in the generated output based on a comparison between the generated output and a corresponding expected output, wherein the corresponding expected output is generated using a goal based modeling technique. Furthermore the method includes identifying by the one or more hardware processors, an optimal policy based on the generated output and the identified deviation using a reward based Reinforcement Learning (RL) model, wherein a policy with maximum reward from among a plurality of policies is identified as the optimal policy, wherein the optimal policy comprises a state-action policy lookup table, and wherein the state-action policy lookup table comprises a plurality of states and an action corresponding to each of the plurality of states. Furthermore, the method includes generating, by the one or more hardware processors, an adaptation specification based on the identified optimal policy using an Adaptation Specification Generation (ASG) technique, wherein the adaptation specification comprises an action name, an action type, an actor, and a plurality of action parameters. Furthermore, the method includes generating, by the one or more hardware processors, a software code dynamically for the identified optimal policy based on the corresponding adaptation specification using an ASG based code generation technique, wherein the software code comprises a plurality of programming instructions required for implementing the identified optimal policy. Finally, the method includes updating, by the one or more hardware processors, the software system under execution by calling a method corresponding to the generated software code and executing the software system.

In another aspect, a system for learning based dynamic software system adaptation is provided. The system includes at least one memory storing programmed instructions, one or more Input/Output (I/O) interfaces, and one or more hardware processors operatively coupled to the at least one memory, wherein the one or more hardware processors are configured by the programmed instructions to receive an output generated by a software system under execution corresponding to a given input, wherein the software system under execution comprises a plurality of states, a plurality of events, a plurality of conditions, a plurality of actions and a plurality of goals. Further, the one or more hardware processors are configured by the programmed instructions to identify a deviation in the generated output based on a comparison between the generated output and a corresponding expected output, wherein the corresponding expected output is generated using a goal based modeling technique. Furthermore the one or more hardware processors are configured by the programmed instructions to identify an optimal policy based on the generated output and the identified deviation using a reward based Reinforcement Learning (RL) model, wherein a policy with maximum reward from among a plurality of policies is identified as the optimal policy, wherein the optimal policy comprises a state-action policy lookup table, and wherein the state-action policy lookup table comprises a plurality of states and an action corresponding to each of the plurality of states. Furthermore, the one or more hardware processors are configured by the programmed instructions to generate an adaptation specification based on the identified optimal policy using an Adaptation Specification Generation (ASG) technique, wherein the adaptation specification comprises an action name, an action type, an actor, and a plurality of action parameters. Furthermore, the computer readable program, when executed on a computing device, causes the computing device to generate a software code dynamically for the identified optimal policy based on the corresponding adaptation specification using an ASG based code generation technique, wherein the software code comprises a plurality of programming instructions required for implementing the identified optimal policy. Finally, the one or more hardware processors are configured by the programmed instructions to update the software system under execution by calling a method corresponding to the generated software code and executing the software system.

In yet another aspect, a computer program product including a non-transitory computer-readable medium having embodied therein a computer program for learning based dynamic software system adaptation is provided. The computer readable program, when executed on a computing device, causes the computing device to receive an output generated by a software system under execution corresponding to a given input, wherein the software system under execution comprises a plurality of states, a plurality of events, a plurality of conditions, a plurality of actions and a plurality of goals. Further, the computer readable program, when executed on a computing device, causes the computing device to identify a deviation in the generated output based on a comparison between the generated output and a corresponding expected output, wherein the corresponding expected output is generated using a goal based modeling technique. Furthermore, the computer readable program, when executed on a computing device, causes the computing device to identify an optimal policy based on the generated output and the identified deviation using a reward based Reinforcement Learning (RL) model, wherein a policy with maximum reward from among a plurality of policies is identified as the optimal policy, wherein the optimal policy comprises a state-action policy lookup table, and wherein the state-action policy lookup table comprises a plurality of states and an action corresponding to each of the plurality of states. Furthermore, the computer readable program, when executed on a computing device, causes the computing device to generate an adaptation specification based on the identified optimal policy using an Adaptation Specification Generation (ASG) technique, wherein the adaptation specification comprises an action name, an action type, an actor, and a plurality of action parameters. Furthermore, the computer readable program, when executed on a computing device, causes the computing device to generate a software code dynamically for the identified optimal policy based on the corresponding adaptation specification using an ASG based code generation technique, wherein the software code comprises a plurality of programming instructions required for implementing the identified optimal policy. Finally, the computer readable program, when executed on a computing device, causes the computing device to update the software system under execution by calling a method corresponding to the generated software code and executing the software system.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

Conventional software adaptation architectures can adapt only non-functional requirements (NFRs) of software like latency, response time and performance using a static repository of knowledge. Functional adaptation of software systems based on real time need, in a dynamic uncertain environment, by continuously refining the knowledge remains mostly unaddressed. Some examples of functional adaptation in software systems include: (i) A telco personalizing product features and customer care services based on changes in customer characteristics, (ii) A bank adjusting parameters used to compute Non-Performing Assets (NPA) risk based on changes in customer characteristics, and (iii) An insurance company changing policy premium based on changes in customer characteristics and the like.

Embodiments herein provide a method and system for learning based dynamic software system adaptation. The present disclosure provides a solution for dynamically adapting functional requirements of software systems by generating necessary software code. Initially, the system receives an output generated by a software system under execution corresponding to a given input. Further, a deviation in the generated output is identified based on a comparison between the generated output and a corresponding expected output, wherein the corresponding expected output is generated using a goal based modeling technique. After identifying the deviation, an optimal policy is identified based on the generated output and the identified deviation using a reward based Reinforcement Learning (RL) model, wherein a policy with maximum reward is identified as optimal policy. The optimal policy includes a state-action policy lookup table, and the state-action policy lookup table includes a plurality of states and an action corresponding to each of the plurality of states. Further, an adaptation specification is generated based on the identified optimal policy using an Adaptation Specification Generation (ASG) technique, wherein the adaptation specification comprises an action type, an actor and a plurality of action parameters. Post generating the adaptation specification, a software code is generated dynamically for the identified optimal policy based on the corresponding adaptation specification using an ASG based code generation technique, wherein the software code comprises a plurality of programming instructions required for implementing the identified optimal policy. Finally, the software system under execution is updated dynamically by calling a method corresponding to the generated software code and executing the software system.

Figure 1:
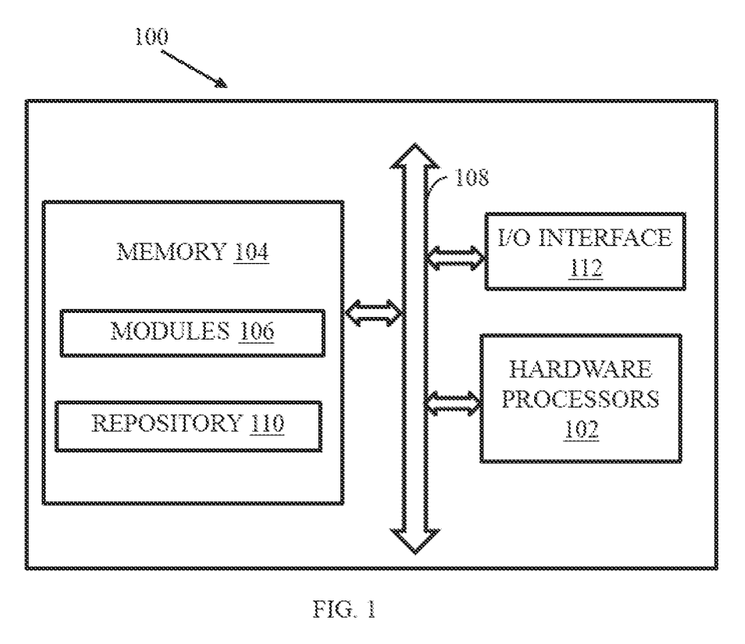
FIG. 1 is a functional block diagram of a system for learning based dynamic software system adaptation, in accordance with some embodiments of the present disclosure.
Figure 2:
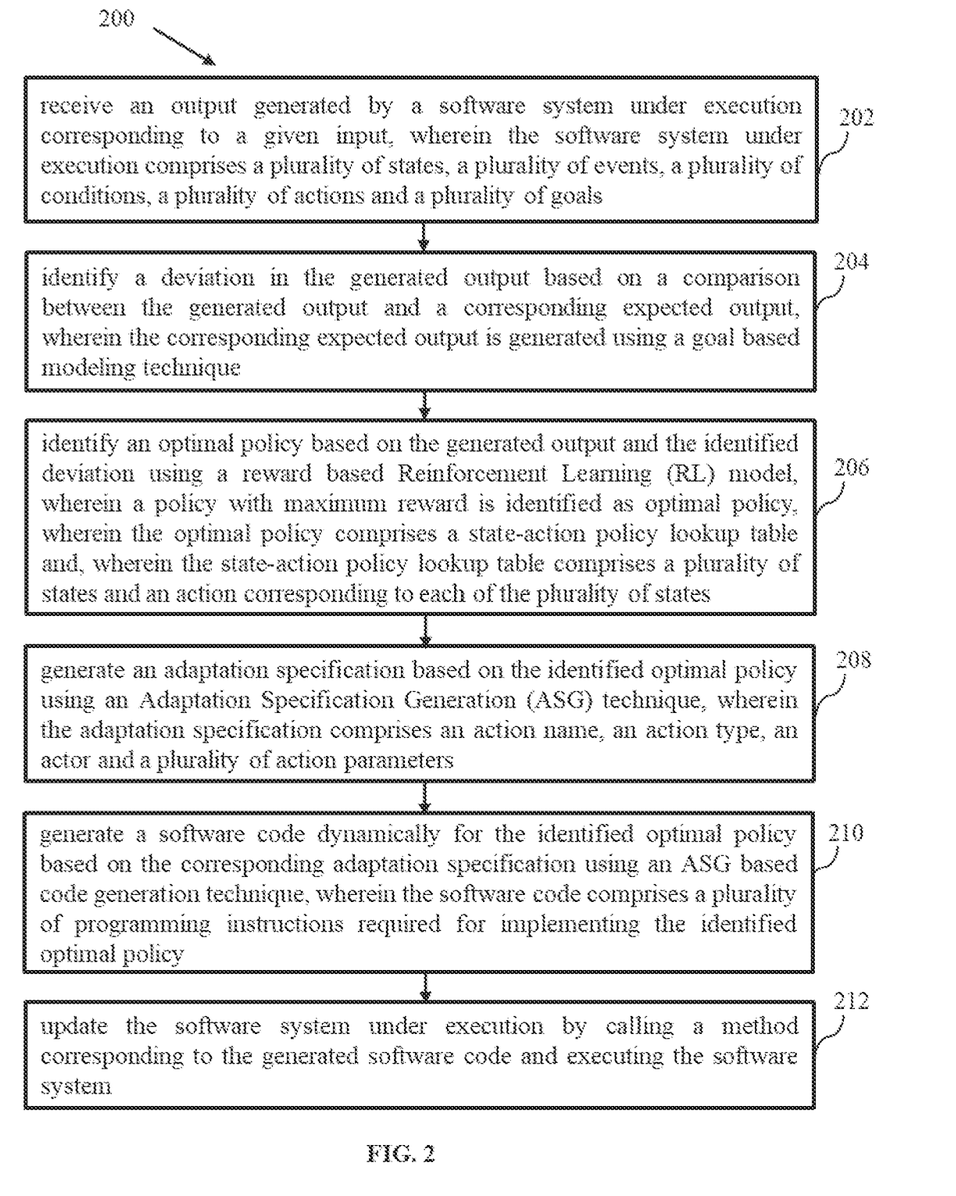
FIG. 2 is an exemplary flow diagram illustrating a processor implemented method for learning based dynamic software system adaptation, implemented by the system of FIG. 1, in accordance with some embodiments of the present disclosure.
Figure 3:
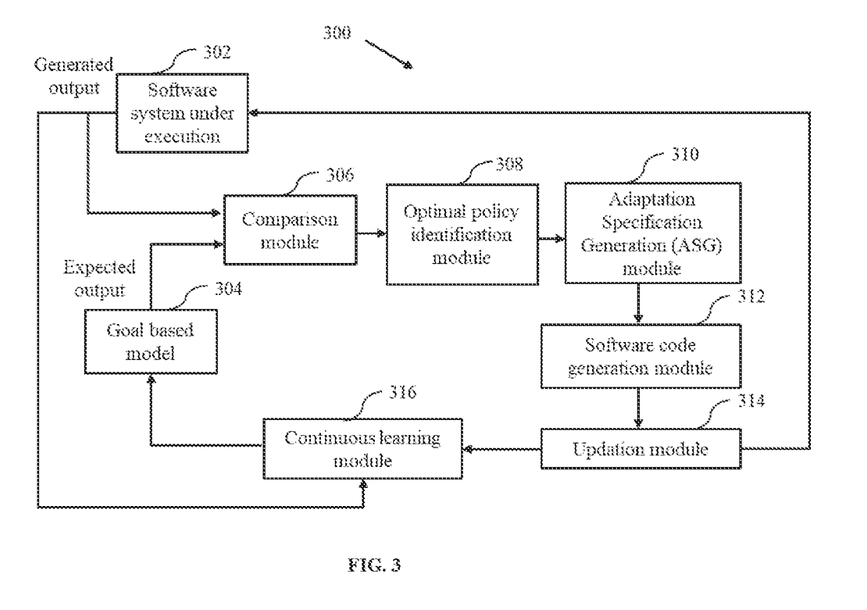
FIG. 3 is an overall functional architecture for the processor implemented method for learning based dynamic software system adaptation implemented by the system of FIG. 1, in accordance with some embodiments of the present disclosure.

Referring now to the drawings, and more particularly to FIGS. 1 through 3, where similar reference characters denote corresponding features consistently throughout the figures, there are shown preferred embodiments and these embodiments are described in the context of the following exemplary system and/or method.

FIG. 1 is a functional block diagram of an onboard system connected to a mobile robot for learning based dynamic software system adaptation, in accordance with some embodiments of the present disclosure. The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a plurality of modules 106. The memory 104 also includes a data repository (or repository) 110 for storing data processed, received, and generated by the plurality of modules 106.

The plurality of modules 106 include programs or coded instructions that supplement applications or functions performed by the system 100 for learning based dynamic software system adaptation. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for the learning based dynamic software system adaptation. In an embodiment, the plurality of modules 106 includes a software system under execution (shown in FIG. 3), a goal based model (shown in FIG. 3), a comparison module (shown in FIG. 3), an optimal policy identification module (shown in FIG. 3), an Adaptation Specification Generation (ASG) module (shown in FIG. 3), a software code generation module (shown in FIG. 3), an updation module (shown in FIG. 3) and a continuous learning module (shown in FIG. 3).

The data repository (or repository) 110 may include a plurality of abstracted piece of code for refinement and data that is processed, received, or generated as a result of the execution of the plurality of modules in the module(s) 106.

Although the data repository 110 is shown internal to the system 100, it will be noted that, in alternate embodiments, the data repository 110 can also be implemented external to the system 100, where the data repository 110 may be stored within a database (repository 110) communicatively coupled to the system 100. The data contained within such external database may be periodically updated. For example, new data may be added into the database (not shown in FIG. 1) and/or existing data may be modified and/or non-useful data may be deleted from the database. In one example, the data may be stored in an external system, such as a Lightweight Directory Access Protocol (LDAP) directory and a Relational Database Management System (RDBMS).

FIG. 2 is an exemplary flow diagram illustrating a method 200 for learning based dynamic software system adaptation implemented by the system of FIG. 1 according to some embodiments of the present disclosure. In an embodiment, the system 100 includes one or more data storage devices or the memory 104 operatively coupled to the one or more hardware processor(s) 102 and is configured to store instructions for execution of steps of the method 200 by the one or more hardware processors 102. The steps of the method 200 of the present disclosure will now be explained with reference to the components or blocks of the system 100 as depicted in FIG. 1 and the steps of flow diagram as depicted in FIG. 2. The method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communication network. The order in which the method 200 is described is not intended to be construed as a limitation, and any number of the described method blocks can be combined in any order to implement the method 200, or an alternative method. Furthermore, the method 200 can be implemented in any suitable hardware, software, firmware, or combination thereof.

At step 202 of the method 200, the one or more hardware processors 102 are configured by the programmed instructions to receive the output generated by the software system under execution 302 (Shown in FIG. 3) corresponding to a given input. The software system under execution includes a plurality of states, a plurality of events, a plurality of conditions, a plurality of actions and a plurality of goals.

For example, the software system under execution is a fitness provider that services fitness requirements of users, a base fitness plan (alternately referred to as 'base plan') is created by the system that needs to be adapted to personalize it according to each user's goals and behavior. The fitness provider monitors the progress of users continuously to understand the changes required.

In an embodiment, the system state of the fitness provider includes the fitness plan provided to at least one user's actual exercise log data at any given point. The events handled by the fitness provider include user registering for fitness services, fitness assessment of the user, creation of the base plan, the user starting the exercise program, etc. The plurality of constraints/conditions checked by the fitness provider at various points of time includes age of the user, lifestyle of the user (sedentary/active/very active), and underlying health conditions of the user.

The plurality of actions associated with the fitness provider includes registration of the users, creation of fitness plan, updation of fitness plan, sending reminders or alerts to the user, etc. The plurality of goals of the fitness provider includes providing optimized fitness plans to meet individual fitness goal of the user such as weight loss, keeping fit, and fitness provider goals such as efficient utilization of resources.

At step 204 of the method 200, the comparison module executed by the one or more hardware processors 102 is configured by the programmed instructions to identify any deviation in the generated output based on the comparison between the generated output and the corresponding expected output. The corresponding expected output is generated using the goal based modeling technique. For example, the goal based model 304 (Shown in FIG. 3) is a knowledge model manifested in the form of a System, Environment & Goal (SEG) Model that symbolizes a hi-fidelity machine-processable representation of the software system (i.e., its digital twin). This knowledge not only represents the current understanding about the problem, domain and the solution but also continuously updates via behavioral learning and refinement throughout the software's life cycle. Further, the digital twin learns from external knowledge sources.

For example, the expected goal or output of weight loss regime is further specified as the measurable sub-goal of "burning 300 calories per day". Burning less than 300 calories per day or burning more than 300 calories per day results in deviation. A user who does only a few numbers of exercises recommended in the plan might burn 180 calories in his workout, resulting in a deviation by 120 calories from his goal.

At step 206 of the method 200, the optimal policy identification module executed by the one or more hardware processors 102 is configured by the programmed instructions to identify the optimal policy based on the generated output and the identified deviation using the reward based Reinforcement Learning (RL) model. A RL agent associated with the RL model interacts with the SEG model in a learning loop guided by the expected goals. In an embodiment, the reward based RL model is trained using a Deep Deterministic Policy Gradient (DDPG) technique. The policy with maximum reward is identified as optimal policy. The optimal policy includes a state-action policy lookup table, and the state-action policy lookup table includes a plurality of states and an action corresponding to each of the plurality of states as shown in Table I).

TABLE I

| State | Action |
| --- | --- |
| {Fitness plans as a sequence of exercises for last 8 weeks, Logs as exercises done along with sets, reps, and duration for last 8 weeks, current week's plan, current week's log} | updatePlan (<exercise, exercise duration, exercise frequency (sets)>,) or send notification to the user for which the action in the policy table will be sendAlert (alertType=" Notification", alertMessage=", " Congratulations on following the plan well! Follow completely for best results.") |

TABLE I-continued

| State | Action |
| --- | --- |
| | or sendAlert (alertType=" Warning", alertMessage=", "You seem to have been missing workouts . . . please resume to avoid plan lapsing!") |

At step 208 of the method 200, the ASG module executed by the one or more hardware processors 102 is configured by the programmed instructions to generate the adaptation specification based on the identified optimal policy using the ASG technique. The adaptation specification includes an action name, an action type, an actor, and a plurality of action parameters, corresponding to each of a plurality of action. The action type includes a parameter value change, a parameter addition, a parameter deletion, a function call, an assignment statement, a condition statement, a precondition, a post condition and a loop statement. The actor associated with the adaptation specification maps to the class (object oriented concept) owning the method in the software system under execution. For each action type, the plurality of action parameters holds appropriate data. For example, for the action Type FunctionCall, the plurality of action parameters are arguments of the method to be called. The action type ParameterAddition includes the plurality of action parameter to be added and the position in the method argument list at which to add. The action type Precondition includes a condition to be added as a predicate over state variables.

The SEG model includes the plurality of actions or methods that are mapped to a method, belonging to a class in the code of the software system under execution. Each action has parameters that are mapped to variables in the SEG model. The plurality of action parameters of the SEG corresponds to method parameters in the code of the software system under execution.

In an embodiment, the ASG translates the optimal policy into the adaptation specification by referring the SEG model using the next action obtained from the state-action policy lookup table.

For example, the ASG looks up SEG model with the action name updatePlan to get associated system method name (GeneratePlan), actor (User class), actionType (ParameterValueChange), and parameters as (exercise, exercise duration, exercise frequency, . . . ) and generates the adaptation specification as generatePlan (ParameterValueChange, User, Exercise, Exercise duration, Exercise frequency, . . . ).

At step 210 of the method 200, the software code generation module executed by the one or more hardware processors 102 is configured by the programmed instructions to generate the software code dynamically for the identified optimal policy based on the corresponding adaptation specification using the ASG based code generation technique. The software code includes the plurality of programming instructions required for implementing the identified optimal policy.

In an embodiment, the adaptation specification is translated to a call using the effectAdaptation method as "effectAdaptation ("generatePlan", "User", exerciseList)". The sample pseudocode for the effectAdaptation method is given below.

```
void effectAdaptation (String methodName, String class-
Name, Object[ ] params)
{
    Class<?> c=Class.forName(className);
    Object obj=c.newinstance( )
    Method[ ] allMethods=c.getDeclaredMethods( )
    for (Method m: allMethods) {
        String mname=m.getName( )
        if (mname.startsWith(methodName))
        Object o=m.invoke(obj, params);
    }
}
```

In an embodiment, the method of generating the software code dynamically for the identified optimal policy based on the corresponding adaptation specification using the ASG based code generation technique includes the following steps. Initially, a current state of the software system under execution is obtained by querying an in-memory system variable value space associated with the software system under execution. For example, the current state includes a plurality of runtime variables associated with the software system under execution. Further, a next action is selected based on the current state using the state-action policy lookup table. After selecting the next action, a method corresponding to the next action is identified from a plurality of methods associated with the software system under execution using a reflection technique. The reflection technique identifies a handle associated with the corresponding method at runtime. The handle is a typed and directly executable reference to an underlying method, for example, constructors in object oriented programming. Further, the identified method is updated with the corresponding adaptation specification corresponding to the next action if the method corresponding to the next action preexist in the software system. If the method corresponding to the next action does not exist in the software system, the software code corresponding to the identified method is generated dynamically based on the next action and the corresponding adaptation specification using a code generation technique. Further, the generated code is compiled and attached to the referenced class at runtime using reflection.

For example, if there is a need to update a policy, the present disclosure verifies whether the particular method exists using reflection technique. The reflection technique is used to extract information from a system at runtime. If the method is already available, the above method is called using a method call with the appropriate parameter values as generated in the adaptation specification, to implement the change in the system code. If the method is not available in the system under execution, the method is created by generating the corresponding software code based on the corresponding adaptation specification.

For example, if the fitness provider wants to send an alert to the user, it is verified whether the corresponding method exist using reflection technique. If the method does not exist in the system, a corresponding code (shown below) is generated and attached to the corresponding user's class and further executed.

```
sendAlert(String alertType, String alertMessage)
{
    If (alertType=="Notification")
        DisplayMessage("Information", alertMessage)
    else if (alertType=="Warning")
        DisplayMessage("Attention!", alertMessage)
    else if (alertType=="Critical")
        DisplayMessage("Urgent Attention!", alertMessage)
}
```

At step 212 of the method 200, the updation module executed by the one or more hardware processors 102 is configured by the programmed instructions to update the software system under execution dynamically by calling the method corresponding to the generated software code and executing the software system.

FIG. 3 is an overall functional architecture for the processor implemented method for learning based dynamic software system adaptation implemented by the system of FIG. 1, in accordance with some embodiments of the present disclosure.

The continuous learning module 316 of FIG. 3 obtains an execution trace by executing the updated software system under execution and updates the corresponding goal based modelling technique continuously based on the execution trace.

In an embodiment, the present disclosure is experimented in wellness system. For example, one's health condition may depend on the one's fitness regime or nutrition intake and vice-versa. Furthermore, these individual requirements are not static and can dynamically change with time or life events or uncertainty in the environment like a pandemic. Even, the stakeholders who serves the need of the consumers have their own goals and would like to remain profitable at all times. Instead of the consumer subscribing to each of the service providers to meet his/her need we envision the notion of a wellness provider that serves as a key integrator of various individual needs under one single umbrella. Thus, the wellness platform becomes a complex interconnected ecosystem of multiple stakeholders where dynamism in goals and uncertainty in the environment are key attributes.

In an embodiment, the present disclosure experimented with the fitness provider system generates a base fitness plan as shown in Table II. the base fitness plan recommends exercises for the user, monitoring the user's actual exercise logs on a weekly basis, and recommends necessary changes to the plan for following week, in order to meet their calorie, burn goal. A sample output of the said experimentation is shown in Table II.

TABLE II

| Exercise | Week 1-Plan | RL recom. for Week 2 | Week 2 updated plan | Week 2 log | RL recom. for week 3 | Week 3 updated plan |
|---|---|---|---|---|---|---|
| 0 Treadmill |  | 0.66166150 | 3 | 1 | 0.655309796 | 3 |
| 1 Elliptical | 1 | 0.68112802 |  |  | 0.562176228 |  |
| 2 Cycling |  | 0.65202534 |  | 1 | 0.687678099 | 3 |
| 3 Walking | 1 | 0.87438464 | 1 |  | 0.508475363 |  |
| 4 Running | 3 | 0.674052 | 4 | 5 | 0.964277029 | 4 |
| 5 Aerobics |  | 0.52143150 |  | 2 | 0.633946657 |  |
| 6 Zumba | 4 | 0.71879023 | 4 |  | 0.570938468 | 2 |
| 7 Bar bells | 1 | 0.79082858 | 3 | 1 | 0.95412904 | 3 |

TABLE II-continued

| | Exercise | Week 1-Plan | RL recom. for Week 2 | Week 2 updated plan | Week 2 log | RL recom. for week 3 | Week 3 updated plan |
|---|---|---|---|---|---|---|---|
| 8 | Dumb bells | 1 | 0.77539610 | 3 | 1 | 0.810546458 | 3 |
| 9 | Bench press | 1 | 0.86076927 | 3 | 1 | 0.982518315 | 3 |
| 10 | Shoulder press | 1 | 0.89489185 | 3 | 1 | 0.763299108 | |
| 11 | Pushups | 1 | 0.78895938 | | 1 | 0.81809628 | 3 |
| 12 | Jumping jacks | 1 | 0.51073193 | | 1 | 0.762722552 | 3 |
| 13 | Squats | 1 | 0.94774377 | 3 | 1 | 0.933125854 | 3 |
| 14 | Forward Lunges | 1 | 0.60390496 | | 1 | 0.91143322 | 3 |
| 15 | Lateral Lunges | 1 | 0.90964543 | 3 | 1 | 0.615597248 | |
| 16 | ReverseLunges | 1 | 0.79762911 | 3 | 1 | 0.997781754 | 3 |
| 17 | Leg Press | 1 | 0.68845593 | | 1 | 0.675783813 | |
| 18 | Leg Extensions | 1 | 0.97630721 | 3 | 1 | 0.573201239 | |

Now referring to Table II, Column 3 shows the base plan with prescribed number of sets for each exercise, Column 4 gives the recommendation weightages by the RL agent for each exercise, which is then converted into an appropriately modified exercise plan for the following week shown in Column 5. Column 6 shows the actual sets performed by the user against each exercise. Columns 7 and 8 give the following week's recommendations based on user's behavior that is input to the RL agent as the current state.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address the unresolved problem of dynamically adapting functional requirements of a software system under execution and thereby improving the non-functional requirements too. The dynamic adaptation is obtained using a unique dynamic code generation technique to correct the deviation from the system under execution from its digital twin. Here an optimal policy for correcting the deviation is obtained using RL based model which is trained using DDPG technique.

It is to be understood that the scope of the protection is extended to such a program and in addition to a computer-readable means having a message therein such computer-readable storage means contain program-code means for implementation of one or more steps of the method when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs, GPUs and edge computing devices.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise. Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e. non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:
receiving, by one or more hardware processors, an output generated by a software system under execution corresponding to a given input, wherein the software system under execution comprises a plurality of states, a plurality of events, a plurality of conditions, a plurality of actions, and a plurality of goals;
identifying, by the one or more hardware processors, a deviation in the generated output based on a comparison between the generated output and a corresponding expected output, wherein the corresponding expected output is generated using a goal based modeling technique;
identifying, by the one or more hardware processors, an optimal policy based on the generated output and the identified deviation using a reward based Reinforcement Learning (RL) model, wherein a policy with maximum reward from among a plurality of policies is identified as the optimal policy, wherein the identified optimal policy comprises a state-action policy lookup table, and wherein the state-action policy lookup table comprises a plurality of states and an action corresponding to each state of the plurality of states;
generating, by the one or more hardware processors, an adaptation specification based on the identified optimal policy using an Adaptation Specification Generation (ASG) technique, wherein the adaptation specification comprises an action name, an action type, an actor, and a plurality of action parameters;
generating, by the one or more hardware processors, a software code dynamically for the identified optimal policy based on a corresponding adaptation specification using an ASG based code generation technique, wherein the dynamically generated software code comprises a plurality of programming instructions required for implementing the identified optimal policy; and
updating, by the one or more hardware processors, the software system under execution by calling a method corresponding to the dynamically generated software code and executing the software system.

2. The processor implemented method of claim 1, wherein generating the software code dynamically for the identified optimal policy based on the corresponding adaptation specification using the ASG based code generation technique comprises:
obtaining a current state of the software system under execution by querying an in-memory system variable value space associated with the software system under execution, wherein the current state of the software system under execution comprises a plurality of runtime variables associated with the software system under execution;
selecting a next action based on the current state of the software system under execution using the state-action policy lookup table;
identifying a method corresponding to the next action from a plurality of methods associated with the software system under execution using a reflection technique, wherein the reflection technique identifies a handle associated with the corresponding method at runtime, wherein the handle is a typed and directly executable reference to an underlying method;
updating the identified method with the corresponding adaptation specification corresponding to the next action if the identified method corresponding to the next action preexist in the software system under execution; and
performing a dynamic generation and dynamic compilation of the dynamically generated software code corresponding to the identified method based on the next action and the corresponding adaptation specification using a code generation technique, if the identified method corresponding to the next action does not exist in the software system under execution, wherein the dynamic compiled software code corresponding to the identified method is attached to a referenced class at runtime using the reflection technique.

3. The processor implemented method of claim 1, wherein the action type comprises a value change, a parameter addition, a parameter deletion, a function call, an assignment statement, a condition statement, a precondition, a post condition, and a loop statement.

4. The processor implemented method of claim 1, wherein the reward based RL model is trained using a Deep Deterministic Policy Gradient (DDPG) technique.

5. The processor implemented method of claim 1, wherein the ASG technique translates the identified optimal policy into the adaptation specification based on a mapping between an action from the identified optimal policy and a corresponding action associated with a corresponding goal based model, and wherein the goal based model is a digital twin of the software system under execution.

6. The processor implemented method of claim 1, wherein an execution trace is obtained by executing an updated software system under execution obtained by updating the software system under execution and a corresponding goal based modeling technique is updated based on the execution trace.

7. A system comprising:
at least one memory storing programmed instructions;
one or more Input/Output (I/O) Interfaces; and
one or more hardware processors operatively coupled to the at least one memory, wherein the one or more hardware processors are configured by the programmed instructions to:
receive an output generated by a software system under execution corresponding to a given input, wherein the software system under execution comprises a plurality of states, a plurality of events, a plurality of conditions, a plurality of actions, and a plurality of goals;
identify a deviation in the generated output based on a comparison between the generated output and a corresponding expected output, wherein the corresponding expected output is generated using a goal based modeling technique;
identify an optimal policy based on the generated output and the identified deviation using a reward based Reinforcement Learning (RL) model, wherein a policy with maximum reward from among a plurality of policies is identified as the optimal policy, wherein the identified optimal policy comprises a state-action policy lookup table, and wherein the state-action policy lookup table comprises a plurality of states and an action corresponding to each state of the plurality of states;
generate an adaptation specification based on the identified optimal policy using an Adaptation Specification Generation (ASG) technique, wherein the adaptation specification comprises an action name, an action type, an actor, and a plurality of action parameters;

generate a software code dynamically for the identified optimal policy based on a corresponding adaptation specification using an ASG based code generation technique, wherein the dynamically generated software code comprises a plurality of programming instructions required for implementing the identified optimal policy; and update the software system under execution by calling a method corresponding to the dynamically generated software cade and executing the software system.

8. The system of claim 7, wherein generating the software code dynamically for the identified optimal policy based on the corresponding adaptation specification using the ASG based code generation technique comprises:

obtaining a current state of the software system under execution by querying an in-memory system variable value space associated with the software system under execution, wherein the current state of the software system under execution comprises a plurality of runtime variables associated with the software system under execution;

selecting a next action based on the current state of the software system under execution using the state-action policy lookup table;

identifying a method corresponding to the next action from a plurality of methods associated with the software system under execution using a reflection technique, wherein the reflection technique identifies a handle associated with the corresponding method at runtime, wherein the handle is a typed and directly executable reference to an underlying method;

updating the identified method with the corresponding adaptation specification corresponding to the next action if the identified method corresponding to the next action preexist in the software system under execution; and performing a dynamic generation and dynamic compilation of the dynamically generated software code corresponding to the identified method based on the next action and the corresponding adaptation specification using a code generation technique, if the identified method corresponding to the next action does not exist in the software system under execution, wherein the dynamic compiled software code corresponding to the identified method is attached to a referenced class at runtime using the reflection technique.

9. The system of claim 7, wherein the action type comprises a value change, a parameter addition, a parameter deletion, a function call, an assignment statement, a condition statement, a precondition, a post condition, and a loop statement.

10. The system of claim 7, wherein the reward based RL model is trained using a Deep Deterministic Policy Gradient (DDPG) technique.

11. The system of claim 7, wherein the ASG technique translates the identified optimal policy into the adaptation specification based on a mapping between an action from the identified optimal policy and a corresponding action associated with a corresponding goal based model, and wherein the goal based model is a digital twin of the software system under execution.

12. The system of claim 7, wherein an execution trace is obtained by executing an updated software system under execution obtained by updating the software system under execution and a corresponding goal based modeling technique is updated based on the execution trace.

13. One or more non-transitory computer-readable media storing one or more instructions which, when executed by one or more hardware processors, cause:

receiving an output generated by a software system under execution corresponding to a given input, wherein the software system under execution comprises a plurality of states, a plurality of events, a plurality of conditions, a plurality of actions, and a plurality of goals;

identifying a deviation in the generated output based on a comparison between the generated output and a corresponding expected output, wherein the corresponding expected output is generated using a goal based modeling technique;

identifying an optimal policy based on the generated output and the identified deviation using a reward based Reinforcement Learning (RL) model, wherein a policy with maximum reward from among a plurality of policies is identified as the optimal policy, wherein the identified optimal policy comprises a state-action policy lookup table, and wherein the state-action policy lookup table comprises a plurality of states and an action corresponding to each state of the plurality of states;

generating an adaptation specification based on the identified optimal policy using an Adaptation Specification Generation (ASG) technique, wherein the adaptation specification comprises an action name, an action type, an actor, and a plurality of action parameters;

generating a software code dynamically for the identified optimal policy based on a corresponding adaptation specification using an ASG based code generation technique, wherein the dynamically generated software code comprises a plurality of programming instructions required for implementing the identified optimal policy; and updating the software system under execution by calling a method corresponding to the dynamically generated software cade and executing the software system.

14. The one or more non-transitory computer-readable media of claim 13, wherein generating the software code dynamically for the identified optimal policy based on the corresponding adaptation specification using the ASG based code generation technique comprises:

obtaining a current state of the software system under execution by querying an in-memory system variable value space associated with the software system under execution, wherein the current state of the software system under execution comprises a plurality of runtime variables associated with the software system under execution;

selecting a next action based on the current state of the software system under execution using the state-action policy lookup table;

identifying a method corresponding to the next action from a plurality of methods associated with the software system under execution using a reflection technique, wherein the reflection technique identifies a handle associated with the corresponding method at runtime, wherein the handle is a typed and directly executable reference to an underlying method;

updating the identified method with the corresponding adaptation specification corresponding to the next action if the identified method corresponding to the next action preexist in the software system under execution; and performing a dynamic generation and dynamic compilation of the dynamically generated software code corresponding to the identified method based on the next action and the corresponding adaptation specification using a code generation technique, if the identified method corresponding to the next action does not exist in the software system under execution, wherein the dynamic compiled software code corresponding to the identified method is attached to a referenced class at runtime using the reflection technique.

15. The one or more non-transitory computer-readable media of claim 13, wherein the action type comprises a value change, a parameter addition, a parameter deletion, a function call, an assignment statement, a condition statement, a precondition, a post condition, and a loop statement.

16. The one or more non-transitory computer-readable media of claim 13, wherein the reward based RL model is trained using a Deep Deterministic Policy Gradient (DDPG) technique.

17. The one or more non-transitory computer-readable media of claim 13, wherein the ASG technique translates the identified optimal policy into the adaptation specification based on a mapping between an action from the identified optimal policy and a corresponding action associated with a corresponding goal based model, and wherein the goal based model is a digital twin of the software system under execution.

18. The one or more non-transitory computer-readable media of claim 13, wherein an execution trace is obtained by executing an updated software system under execution obtained by updating the software system under execution and a corresponding goal based modeling technique is updated based on the execution trace.

* * * * *